(12) United States Patent
Sperling et al.

(10) Patent No.: US 9,726,597 B2
(45) Date of Patent: Aug. 8, 2017

(54) APPARATUS AND METHOD OF INVESTIGATING SURFACE PROPERTIES

(71) Applicant: BYK-Gardner GmbH, Geretsried (DE)

(72) Inventors: Uwe Sperling, Geretsried (DE); Peter Schwarz, Geretsried (DE)

(73) Assignee: BYK-GARDNER GMBH (DE)

( * ) Notice: Subject to any disclaimer, the term of this patent is extended or adjusted under 35 U.S.C. 154(b) by 0 days.

(21) Appl. No.: 14/645,831

(22) Filed: Mar. 12, 2015

(65) Prior Publication Data

US 2015/0260641 A1    Sep. 17, 2015

(30) Foreign Application Priority Data

Mar. 17, 2014  (DE) ........................ 10 2014 103 640

(51) Int. Cl.
*G01N 21/25* (2006.01)
*G01N 21/64* (2006.01)
*G01N 21/47* (2006.01)

(52) U.S. Cl.
CPC ......... *G01N 21/251* (2013.01); *G01N 21/474* (2013.01); *G01N 21/645* (2013.01); *G01N 2021/4735* (2013.01); *G01N 2021/4766* (2013.01); *G01N 2021/4783* (2013.01); *G01N 2021/6471* (2013.01); *G01N 2201/062* (2013.01); *G01N 2201/068* (2013.01)

(58) Field of Classification Search
CPC ....... G01N 21/251; G01N 21/474; G01J 3/46; G01J 3/02; G01J 3/51; G01J 3/28
USPC .................................................. 356/300–425
See application file for complete search history.

(56) References Cited

U.S. PATENT DOCUMENTS

| 7,404,929 B2 * | 7/2008 | Fulghum, Jr. ........ | A61B 5/0071 |
| | | | 422/82.05 |
| 2004/0032581 A1 * | 2/2004 | Nikoonahad ...... | G01N 21/9501 |
| | | | 356/237.2 |
| 2005/0033127 A1 * | 2/2005 | Ciurczak ............ | A61B 5/14532 |
| | | | 600/316 |

* cited by examiner

*Primary Examiner* — Abdullahi Nur
(74) *Attorney, Agent, or Firm* — Onello & Mello, LLP.

(57) ABSTRACT

The invention relates to an apparatus for the investigation of surface properties with a housing, a light source which directs light through an opening in the housing onto a surface to be investigated, with a first detector device which is arranged inside at a first pre-set angle with respect to the light beam radiated onto the surface by the light source, with a second detector device which is arranged at a second pre-set angle with respect to the light beam radiated onto the surface by the light source and with a third detector device which is arranged inside the housing at a third pre-set angle with respect to the light beam radiated onto the surface by the light source. According to the invention the apparatus has at least two filter elements with optical properties which are different from each other which are arranged on a common carrier movable with respect to the light source, in such a way that each of these filter elements is optionally capable of being brought into a beam path between the light source and the surface.

25 Claims, 1 Drawing Sheet

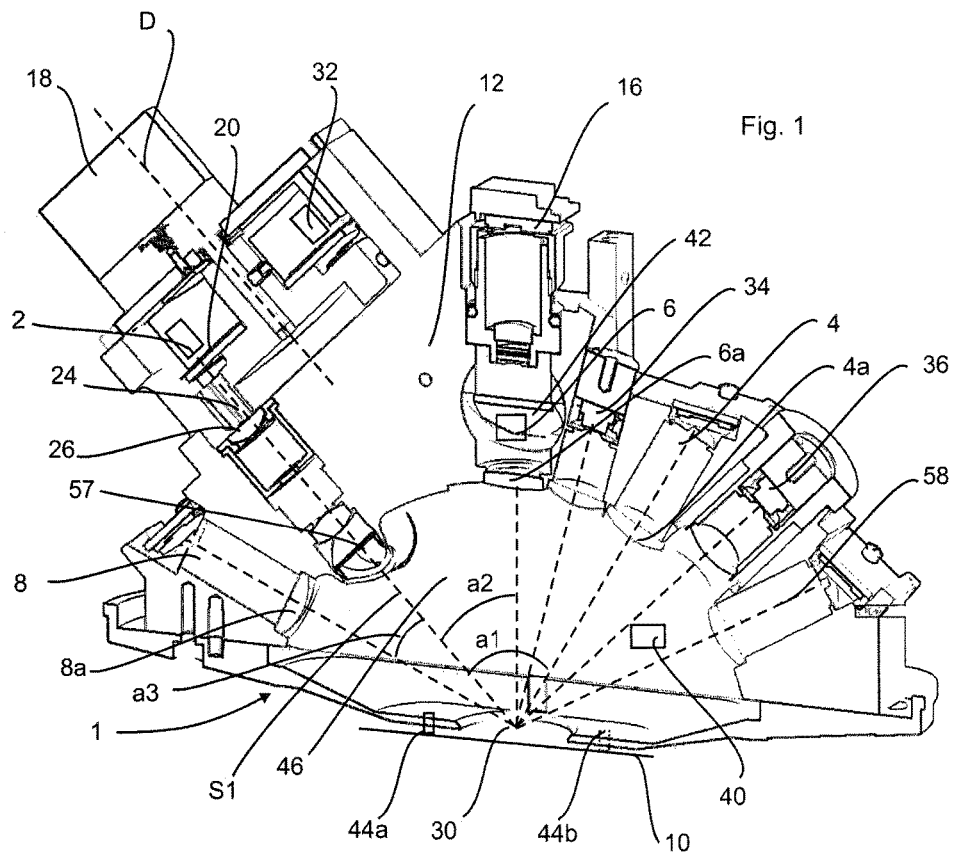
Fig. 1
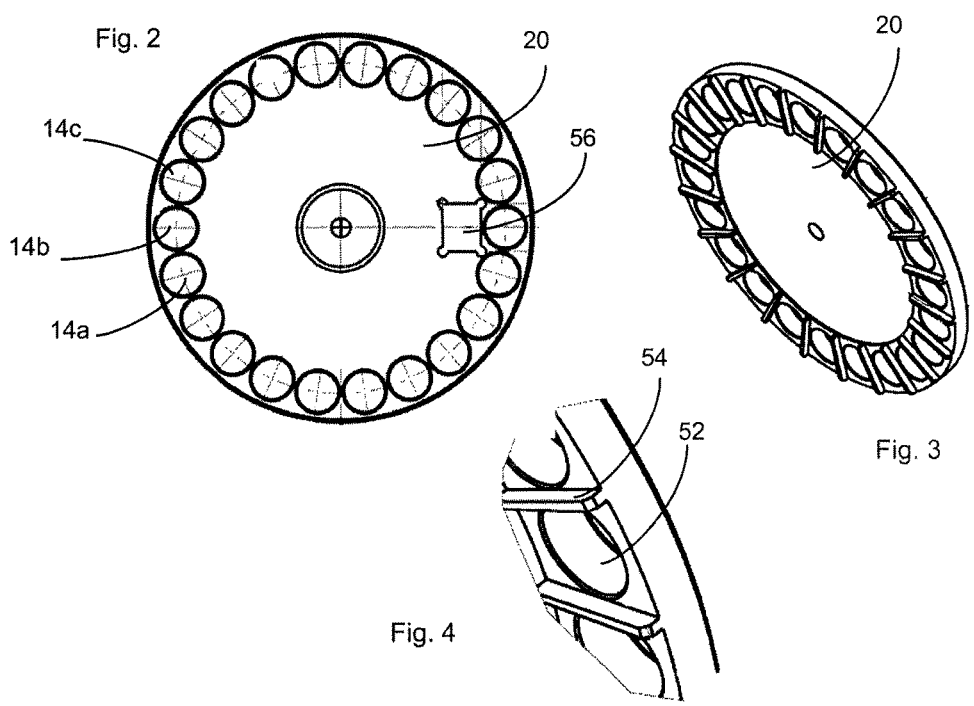
Fig. 2
Fig. 3
Fig. 4

APPARATUS AND METHOD OF INVESTIGATING SURFACE PROPERTIES

RELATED APPLICATIONS

This application claims benefit under 35 USC 119 to German Patent Application Serial Number 102014103640.9, filed Mar. 17, 2014, the content of which is incorporated herein by reference in its entirety.

FIELD

The present invention relates to an apparatus and a method of investigating surface properties, and in particular investigating optical surface properties such as in particular but not exclusively the colour, a colour progression, a surface roughness and the like.

DESCRIPTION OF DRAWINGS

Further advantages and embodiments are evident from the accompanying drawings. In the drawings FIG. 1 is a diagrammatic illustration of an apparatus according to the invention;

FIG. 2 is a plan view of a filter wheel;

FIG. 3 is an oblique view of the filter wheel shown in FIG. 2, and

FIG. 4 is an enlarged illustration of the filter wheel shown in FIG. 3.

DETAILED DESCRIPTION

Apparatus of this type have long been known from the prior art. High-quality surfaces, such as in particular paint of vehicle bodies, frequently have a multiplicity of widely differing optical properties. Under certain conditions it may be helpful for these properties to be determined objectively or for a measure to be obtained as to how these optical properties also act under different illumination. For this reason various apparatus and methods by which these surface properties are capable of being determined are known from the prior art. In this way, US 2007/0206195 describes for example an apparatus for the determination of surface properties. This apparatus has a plurality of detector elements which can detect radiation scattered by a surface to be investigated. Various filter elements can be pushed in each case in front of these detector devices by means of a circulating belt. In this case, however, this apparatus is relatively complicated both to operate and to produce. In addition, as a result of this arrangement, effects such as for example a fluorescence of the surfaces to be determined cannot be detected since the sample is not irradiated successively with light of different wavelength and at the same time the detected light is spectrally resolved.

U.S. Pat. No. 7,433,055 B2 likewise describes an apparatus for the investigation of optical surface properties. This apparatus has in this case a carrier on which a plurality of light sources with different emission spectra are arranged. In this way, it is possible for the stressing of the surfaces to be investigated to be achieved with light of different properties.

This apparatus has the drawback, however, that the individual light sources arranged on the movable carrier have to be supplied with current. In addition, the failure of an individual light source of this type makes it necessary to replace the entire carrier. In the case of the application specified, a precise characterization and selection of the light sources with respect to the emission spectrum is additionally necessary.

The object of the present invention is therefore to make available an apparatus and a method of investigating surface properties, which are simpler to manipulate and produce as compared with apparatus known from the prior art but which also have a lower susceptibility to failure, and in addition provide the possibility of measuring the fluorescence.

This is attained according to the invention by the subjects of the independent claims. Advantageous embodiments and further developments form the subject matter of the subclaims.

An apparatus according to the invention for the investigation of surface properties or for the determination of surface properties respectively has a housing (also referred to as an optical block below) as well as a light source which directs light through an opening in the housing onto a surface to be investigated. In addition, the apparatus has a first detector device which is arranged inside the housing and/or on the housing at a first pre-set angle with respect to the light radiated onto the surface by the light source. In addition, the apparatus has a second detector device which is arranged inside the housing and/or on the housing at a second pre-set angle with respect to the light beam radiated onto the surface by the light source and also a third detector device which is arranged inside the housing and/or on the housing at a third pre-set angle with respect to the light beam radiated onto the surface by the light source.

According to the invention the apparatus has at least two filter elements with optical properties which are different from each other which are arranged on a common carrier movable with respect to the light source, in such a way that each of these filter elements is optionally capable of being brought into a beam path between the light source and the surface.

It is therefore proposed within the scope of the invention that the filter elements should be arranged on the side towards the radiation, i.e. between the light source and the surface to be investigated. At first this procedure seems impractical since in this way a high proportion of the power of the radiated light is removed from the outset by the respective filter element and is no longer available for the measurement. On the other hand, however, this apparatus provides the possibility of working with only one light source or one specific type of light sources respectively. In addition, these light sources can be arranged in a stationary manner and need not therefore be supplied with current on a movable carrier. In this way, the risk of failure can be minimized and, in addition, a replacement of the light source is simpler than in the case of the prior art cited above in which it is also necessary to replace the entire carrier with a plurality of light sources. It is pointed out, however, that the apparatus according to the invention and the method according to the invention are also capable of being used with only two detector devices which record the light reflected and/or scattered by the surface. The third detector device or the third measurement angle respectively, however, contributes to a precise measurement. The Applicants therefore retain the right also to claim the apparatus with only two detector devices.

In addition, it is necessary for the filters to be attached to the primary side only once, but on the secondary side the filter arrangement would be necessary in front of each detector. In addition, as compared with a semiconductor light source for example, interference filters provide the possibility of defining and implementing the spectral radiation characteristic of the illumination in a precise manner. As a result, the edge steepness or overall brightness for example can be determined in advance or secondary maxima can also be generated or suppressed in a deliberate manner. It is preferable for precisely one of the filter elements to be capable of being moved in each case into the beam path of the light between the light source and the surface. It is preferable for two different filter elements to be designed in such a way that if they were positioned in succession in a beam they would allow substantially no light to pass in their joint operation. The pass wavelength ranges of the two filters are preferably clearly differentiated. It is preferable for the apparatus to have more detector devices than radiation devices or light sources respectively or groups of light sources. In this way, the number of sets of filters can be kept low and, in a particularly preferred manner, the operation can be carried out with only one set of filters.

On account of the arrangement of the filter elements on the side towards the radiation and not on the side towards the detector, measurements of the fluorescence of the surface can also be made possible. An arrangement of the detector device inside the optic block is understood as being that although a detector element itself may possibly be situated geometrically outside the optical measurement space, it is preferable for the detector device to be arranged in such a way that radiation originating substantially exclusively from an interior of the optical measurement space, and in particular radiation originating from the surface to be investigated, arrives at the detector device.

It is preferable for the optical measurement space, with the exception of the opening mentioned above by way of which light is radiated onto the surface, to have no further openings through which light from the outside or ambient light respectively can enter the housing. It is preferable for a cavity, into which both the light source and the radiation device in general respectively can radiate, to be formed inside the optical measurement space.

The detector devices are accordingly arranged in such a way that they can detect such radiation as occurs inside this space. In this way, channels through which radiation scattered and/or reflected by the surface arrives at the individual detector devices could be arranged in a wall bounding this space. Optical elements such as lenses, diaphragms, diffusing plates, beam splitters and the like can be arranged in or on these channels. By using these channels, which preferably pass through a wall of the housing at least in part, it is possible for a plurality of detector devices to be arranged adjacent to one another.

It is preferable for the individual detector devices to be arranged in one plane. This means that the radiated light and the light recorded by the detector device are situated in a common plane in each case. A lateral displacement of an individual detector device with respect to this plane would also, however, be possible. In this case it is not necessary, in particular, for the detectors of the fluorescence radiation to be situated in one plane with the radiation source since the fluorescent light which is radiated by a sample is emitted in all directions.

In the case of the apparatus according to the invention the light radiated onto the surface can thus be determined by the surface at different angles, namely at the angles at which the respective detector devices are arranged. In this way, the colour impression of the surface can be observed at different angles of observation. This is also advantageous in particular when the surface to be investigated is an effect-pigmented surface, for example a so-called effect paint into which pigments are incorporated. These can be for example, but not exclusively, aluminium, bronze, interference, mica, pearl and glass pigments or helicons.

It is preferable for the surface properties to be colour properties of the surface to be investigated. In this way, the individual detector devices are also used, in particular, for determining colour properties of the surface.

It is advantageous for the detector devices to be detector devices which are capable of emitting an intensity value of the radiation detected. It would also be possible for detector devices to be used which allow a spatially resolved resolution of the radiation, for example CCD chips or camera elements and the like.

It is preferable for optical elements, such as in particular but not exclusively lenses, diaphragms, beam splitters or diffusing plates, to be arranged between the light source and the filter element. It is preferable for optical elements, such for example lenses, diaphragms, diffusing plates and the like, to be arranged between the filter and the surface to be investigated.

It is preferable for two different filter elements to differ with respect to their wavelength-dependent degrees of transmission, i.e. in a manner dependent upon the wavelength of the light striking these filter elements.

It is also preferable for band-pass filters to be used, which cover the visible spectral range or the spectral range of from 320 to 720 nm at substantially uniform intervals and which have a pass range of for example 10 or 20 nm in each case. It is therefore preferable for the pass range of the individual band-pass filters to be between 5 nm and 30 nm, preferably between 8 nm and 25 nm.

It is preferable for band-pass filters with different pass ranges to be provided, for example in ranges in which the human eye is particularly sensitive smaller pass ranges can be provided, such as in the green colour range of the spectrum.

In the case of a further advantageous embodiment the apparatus has at least one temperature measuring instrument. It is preferable for this to be a temperature measuring instrument which determines the temperature of the light source. The radiation characteristics of light sources of this type also depend upon an operating temperature of this light source. It is also possible for such changes in the radiation characteristics to be taken into consideration by a determination of the temperature. It would further be possible, however, for a measuring instrument to be provided which determines an operating variable characteristic of the light source, such as for example an operating current and/or an operating voltage. A correlated indication of temperature can possibly be determined from these parameters. In addition, it would also be possible for ambient temperatures which can likewise have an effect upon the measurement values to be measured by means of the temperature measuring instrument. Conditions which can falsify the measurement result can be detected and corrected in this way.

It is advantageous for at least one detector device to be a camera, and in a particularly preferred manner a spectral camera. The latter affords the advantage of a spatial resolution of the different colour components or areas respectively of the light reflected by the sample. Although conventional colour cameras achieve a colour impression which acts naturally in front of the eye, they by no means cover the entire existing band width thereof, which is in fact visible light for us. In addition to the spatial resolution, a spectral camera provides a substantially more precise resolution of the colour information.

In addition, a black-and-white camera with n illumination channels of different spectral emissions could also be used.

An RGB camera provides only three wavelength ranges, whereas a camera with an illumination with n discrete wavelengths can investigate a sample with n colour channels. In addition, combinations of the three procedures proposed here are possible.

In this way, it would be possible on the one hand to resort to relatively expensive spectral cameras, but it would also be possible, however, to convert a conventional camera into a spectral camera of this type by an additional structure. In this case it would be possible for light which passes from the photographed object, in this case the surface, to be imaged onto an optical grid by a lens. This grid can be for example a special foil of plastics material. This foil deflects the light beams before they reach the camera, namely to different degrees depending upon the wavelength.

In this way, light of different colours lands on different positions of the camera sensor. The optical properties of the surface are then determined—mathematically or by software respectively—from the measurement data of the sensor. In addition, cameras with a built-in filter wheel can be used.

In the case of a further advantageous embodiment the optical block or the adjoining base plate respectively can have arranged on it sensor devices, such as in particular but not exclusively mechanical sensing devices, which establish whether an ideal position of the appliance with respect to a surface is observed. In this case it is possible for three push switches to be arranged in such a way that when all three push switches are actuated it is possible to assume an ideal positioning of the appliance with respect to the surface.

It is advantageous for the apparatus described here to be used for colour measurements which are used for example to determine colour formulations for example for vehicle bodies or their paint respectively. In addition, the apparatus can also be used for a database search in the case of paints or even in the field of a refinish, in particular but not exclusively in the case of motor vehicles, but optionally also for example in the case of pieces of furniture.

In general, the appliance can be used for the control or analysis of paints or even plastics material surfaces. In addition, it is possible to detect fluorescence or optical brighteners. Frequently in fact, use is made of cheaper fluorescent substances in order to replace expensive colour pigments, in particular white colour pigments, in this way.

In the case of a further advantageous embodiment the apparatus has a measuring instrument which determines distances covered with respect to the surface to be investigated. In this case it is possible for the apparatus to be displaced with respect to the surface and for the path covered to be determined in this case. In this way, it would be possible for one or more wheels to be arranged on the housing, in which case at least one of these wheels is used for the determination of distances.

In the case of a further advantageous embodiment the apparatus has a position detection element which determines a position of the movable carrier with respect to the light source. In this way for example, the carrier can have arranged on it an element which triggers a reaction in a specified position, such as for example a mirror, which in a specified setting directs a signal to a detector, so that the position of the carrier can be detected. A reflection or forked light barrier can also be used in a similar manner. It is also possible, however, for the position of the filter wheel to be determined by a filter with special properties such as for example transmission in the entire visible range, or total blocking in the visible range, or transparency in a precisely defined UV or IR range. The determination is carried out by optical sensing in a detector precisely determined and filtered therefor and a suitable evaluation logic.

In the case of a further advantageous embodiment at least one detector device has an amplifier device which amplifies the signals produced by the detector device in reaction to the incident radiation. In this case this amplifier device can preferably be dependent upon the wavelength, so that different wavelength ranges can be amplified to different degrees. In this way, fluctuations in the wavelength spectrum can be equalized in a purposeful manner by different degrees of amplification in the respective detector device.

In the case of a further advantageous embodiment at least one filter element is a band-pass filter element. A band-pass filter of this type allows only one specified light wavelength range to pass. At the margins of this range the transmission of the filter element preferably drops to a considerable degree. It is preferable for the filter element to allow only parts of less than 1%, preferably of (significantly) less than 0.1% and in a particularly preferred manner of less than 0.05 to pass outside the transmitted wavelength range. For the measurement of fluorescence it may also be advantageous for filters with an optical density of at least 5 (OD 5) to be used. It is therefore advantageous for a plurality of filter elements of this type to be used which transmit different wave ranges of the light or allow them to pass respectively. It is advantageous for these entire filters to cover in their entirety the complete visible range of the light. It is advantageous for the band-pass filter to be a colour filter which advantageously has interference filters. In this way, it is preferable for at least one filter element to have an interference filter.

In the case of a further advantageous embodiment the light source is a light-emitting diode (LED), and in particular a white light LED. It is preferable for this LED to have an output which is preferably in a range of between 1 watt and 5 watts, preferably between 1 watt and 2 watts. It is preferable for the light source to cover at least the entire visible spectrum of the light with its radiation. In addition, the light source can also radiate UV and IR portions of the light. It is particularly preferable for the light source also to cover a range of ultraviolet light adjoining the visible range of the light. It is preferable for this range, starting from the visible wavelength range, to extend at least to 300 nm, preferably at least to 320 nm, preferably at least to 340 nm, and in a particularly preferred manner at least to 360 nm. It is preferable for a continuous range to be covered, starting from these specified wavelengths as far as the visible wavelength range. The visible wavelength range of the light extends from approximately 400 nm to 700 nm.

In this case this LED advantageously has an initial radiation which radiates over the complete visible wavelength range, i.e. approximately between 400 nm and 700 nm. It is advantageous for this wavelength characteristic of the radiated radiation to be taken into consideration both when the filters are made available and in the design of the amplifiers of the individual detector devices. In this way, the amplification factors of the amplifier devices of the individual detector devices can be adapted in a manner dependent upon the respective filter.

It is advantageous for the light source to have a phosphorescent material. This material produces a frequency shift of the light produced or radiated respectively. In this way, a more uniform output spectrum of the light source can be achieved. In this way, the amplification of all the channels can advantageously be brought to a similar level, and this entails a similar noise behaviour. The uniform output spectrum of the lamp can also be achieved by adjustment of the degree of transmission of the filters. In this case the filter is designed in such a way that the product of the LED and the degree of transmission of the filter in any band-pass interval is raised to a similar level or substantially the same level respectively.

In the case of a further advantageous embodiment the described carrier which is movable with respect to the light source is a rotatable wheel. It is advantageous for a plurality of filter elements to be arranged on this wheel, so that they can optionally be displaced into the beam path between the light source and the surface to be investigated. It is preferable for the apparatus to have a motor drive for the filter wheel, so that filters can be displaced in a pre-set sequence between the light source and the surface, in particular in a manner controlled by a program. It is advantageous for the motor drive to be a stepping motor drive. A direct-current motor, however, can also be used. It is preferable for the rotational movement to be measured with a displacement sensor and/or an angle sensor. As a result, the rotational movement can be monitored in a purposeful manner or stopped at specific points, for example at the middle of each filter. The illumination can be activated in a continuous manner during the rotational movement or can be switched on or off in a purposeful manner at each filter.

In addition, the apparatus preferably has a control device for controlling the motor drive. In this case this control device can cause filter elements to be displaced in a pre-set sequence into the beam path between the light source and the surface. It is advantageous for this control device also to control the light source and/or the individual detector devices. In this way, in the scope of a measurement sequence for example a measurement can first be carried out with a plurality of detector devices whilst using a first filter element and a measurement can then be carried out whilst using a further filter element.

In the case of a further advantageous embodiment the apparatus has a second light source which likewise directs light onto the surface to be investigated. This second light source can be arranged inside the measurement plane at a different illumination angle from the first light source. From this second light source it would be possible to detect further optical properties of the surface, for example an increased colour progression determination over a further angular range, the colour distributions, colour flops, brightness flops, gloss, haze, orange peel and the like.

It is preferable for at least one filter element also to be capable of being brought into a beam path between the second light source and the surface to be investigated. In this case it is possible for this filter element to be arranged on the same carrier as those filter elements which can be displaced between the first light source and the surface. In addition, it is possible for specific filter elements on the carrier to be displaced both into the beam path between the first light source and the surface and into the beam path between the second light source and the surface. It is advantageous for all the filter elements to be capable of being displaced or of being moved respectively both into the beam path between the first light source and the surface and into the beam path between the second light source and the surface.

In addition, the provision of a further light source also allows the radiation of light at different angles (with respect to the surface).

In this case it is preferable for the first light source and then the second light source to be activated in an alternating manner, different filters in each case being displaced into the beam path.

In a further application it would be possible for the light source, for example the white LED, to be arranged above the filter wheel. In the case of a further advantageous embodiment the apparatus has both detector devices which allow an integral colour measurement, and detector devices which allow a spatially resolved determination of the light scattered or reflected respectively. In this way, the non-homogeneity of the paint surface which is achieved for example by effect pigments can be measured more precisely and resolved spatially.

In the case of a further advantageous embodiment the apparatus has a beam splitter device between the surface to be investigated and at least one detector device. In this way for example, a beam splitter which allows the decoupling of a reference beam path can be provided in the case of the illumination lens, in order to measure an intensity of illumination or a spectrum for example. This signal measured accordingly can in turn be used for the calibration or the measurement correction of the apparatus.

In the case of a further advantageous embodiment the apparatus has a fluorescence measuring instrument. This fluorescence measuring instrument or even fluorescence measuring channels respectively can be arranged per se in any desired regions of the optic block as a whole or the housing respectively. It is advantageous, however, for these sensor devices to be directed onto the surface to be investigated. It is preferable for at least one fluorescence measuring instrument of this type to be arranged on a lateral wall of the housing, preferably above a measurement area or above the surface to be investigated respectively. The fluorescence measuring instrument preferably has a plurality of channels which react—preferably by way of filters—to different wavelength ranges. In this way, the sample can be illuminated with different wavelength ranges of the illumination and in this way the occurrence of fluorescence of the sample can be measured with the fluorescence detectors. The fluorescence measuring instrument can also be implemented with a spectrometer component for example on the basis of a grid or prism. It is preferable therefore for the fluorescence measuring instrument to be suitable and intended for recording a multiplicity of wavelength ranges of the light to be detected, preferably independently of one another, and preferably also for evaluating them.

The fluorescence measuring instrument can likewise in this case be incorporated in a wall of the housing. In this case a channel through which fluorescence radiation can arrive at the fluorescence measuring instrument from the surface can likewise be arranged in the housing wall. It is preferable, however, for the fluorescence measuring instrument to be arranged in such a way that it detects exclusively radiation originating in the surface to be investigated.

As mentioned above, the housing has a cavity or measuring space respectively into which the light source radiates. In this case a wall bounding this cavity can preferably be made radiation-absorbing. In this way, it is possible for the detector device to reach light originating substantially only from the surface.

If elements reflecting in a diffuse manner or elements illuminating in a diffuse manner, which can be used for producing a diffuse light and thus for illuminating the sample in a diffuse manner, are attached to the wall of the optic block or the optical measuring space respectively, then it is necessary to ensure structurally that no light or very little light passes from these diffuse areas directly into the detector devices.

The present invention further relates to a method of investigating surface properties or of determining surface properties respectively. In this case light is radiated by means of a light source through an opening in a housing or measuring space respectively onto a surface to be investigated and the light reflected and/or scattered by the surface as a consequence of this radiation is detected with a first detector device at a first pre-set angle with respect to the light radiated from the light source onto the surface, is detected with a second detector device and a second pre-set angle with respect to the light beam radiated from the light source onto the surface and is detected by means of a third detector device at a third pre-set angle with respect to the light beam radiated from the light source onto the surface.

According to the invention, while the method is carried out, at least two filter elements with mutually different optical properties, which are arranged on a common carrier movable with respect to the light source, are brought into a beam path between the light source and the surface in a manner staggered in time, so that only one filter element of these two filter elements is present in this beam path in each case.

It is therefore also proposed in terms of the method that filter elements should be positioned in the beam path on the side towards the radiation. As mentioned above, these are preferably filter elements which allow only specified wavelength ranges to pass. It is advantageous for a plurality of filter elements to be positioned in the beam path between the light source and the surface during the measurement.

It is preferable for image recordings or intensity measurements respectively to be carried out with each of these filter elements (in the beam path) by at least one detector device and preferably by all the detector devices. In this way, in order to determine the surface by the radiation with light of different wavelengths and the recording of the reflected or scattered radiation resulting from this surface is investigated in particular with respect to the colour properties or the occurrence of fluorescence thereof.

In this way, it is advantageous for the surface properties to be colour properties of the surface to be investigated. It is advantageous for the surface to be a layer of paint, in particular a layer of paint of a vehicle. It is advantageous for the surface further to be a layer of paint having effect pigments. On account of this procedure a brightness flop or a colour flop or absolute colour values can be determined for example by means of an L, a, b scale. Effect pigments can be characterized with respect to their colour, the size, the radiation intensity of the entire surface or the like.

In the case of a further preferred method fluorescence radiation is detected at least for a time. This is, in particular, fluorescence radiation originating in the surface to be investigated. It is advantageous for this fluorescence radiation to be recorded by a further radiation detection device. In the case of a further preferred method this fluorescence radiation can be recorded at the same time as another radiation at least for a time.

In the case of a further advantageous method the surface to be investigated is also illuminated with a further light source. It is preferable in this case for this second light source to be independent of the first light source and, in particular, also to be capable of being controlled independently of the first light source. It is advantageous for a filter element also to be arranged between the second light source and the surface. Further advantages and embodiments are evident from the accompanying drawings.

FIG. 1 is a diagrammatic illustration of an apparatus 1 according to the invention for the investigation of optical properties of a surface 10. This apparatus 1 has an optic block 12 in which a plurality of different measuring instruments are provided and which encloses a measuring space. In this case the reference number 2 designates a light source which emits light and radiates along the broken line S1 (i.e. of the light beam striking the surface 10) through an opening 30 of the measuring space onto the surface 10. The light thrown back, i.e. in particular scattered and/or reflected, by this surface 10 is recorded by a plurality of detector devices.

In this way, the reference number 4 designates a first detector device which records radiation which arrives at an angle a1, determined with respect to the radiation direction S1, and which is reflected and/or scattered by the surface 10. The reference number 6 designates a second detector device which records light scattered by the surface 10 at the angle a2. The reference number 8 designates a third detector device which records radiation scattered at the angle a3. In this way, the surface 10 is observed at different angles, since this observation at the different angles is characteristic as a whole of the optical impression of the surface 10.

The individual detector devices 4, 6 and 8 in each case emit values which are characteristic of an intensity of the radiations arriving at these detector devices. The optical impression of the surface 10 can be determined at different angles of observation with reference to these intensity values. The detector device 6 is illustrated only diagrammatically in this case since it is not situated in the plane shown in FIG. 1 but is offset laterally with respect to this plane. The reference number 58 designates a further (fourth) radiation detector device, which is arranged at a further angle to the radiation device.

A filter wheel 20, which has a plurality of filter elements, is provided between the light source 2 and the surface 10, i.e. in the region of the beam path S1. In this case the reference letter D designates the axis of rotation about which the filter wheel is rotated. This axis of rotation is substantially parallel in this case to the beam direction S1, substantially parallel being understood as being that the direction of the axis of rotation and the beam direction S1 differ from each other by not more than 15°, preferably by not more than 5°, and in a particularly preferred manner by not more than 3°. The reference number 46 designates the interior of the optic block 12. In this case the interior can be made hemispherical or even hemi-elliptical. Radiation occurring in this interior 46 can arrive at the individual detector devices.

As a result of a change in the rotational setting of this filter wheel 20 the different filters can be moved or displaced respectively into the beam path between the light source 2 and the surface 10. The reference number 24 designates a channel which adjoins the filter element and through which the light passes.

The reference number 26 designates an optical element, such as a lens, which influences the beam.

The reference number 18 designates a drive device, such as a motor which can vary the rotational setting of the filter wheel 20. This motor can be actuated in this case within the scope of a measurement procedure, so that specified filter elements can be displaced into the beam path in a purposeful manner.

In addition, the individual detector devices 4, 6 and 8 in each case have lenses 4a, 6a and 8a. The reference number 16 refers to an image recording device which in this case is arranged vertically above the surface. A specific portion of the light arriving at detector device 16 from the surface can be decoupled by means of a beam splitter 42 for an additional integral colour measurement for example.

The reference number 34 designates a further illumination device which is used for the illumination of the sample for a spatially resolved detection. The references 44a and 44b indicate two sensing devices which are arranged on the underside of the housing. When the apparatus is positioned correctly with respect to the surface 10, the two sensing elements 44a and 44b are actuated, but also as well as a further sensing element (not shown).

The reference number 36 designates a further illumination device which illuminates the measurement spot. This illumination device is situated for example at the angle of reflection of the light radiated from the light source 2 and acts at the same time as a light trap for the directly reflected radiation of the illumination source 2.

The reference number 40 designates a fluorescence detection device which in this case, however, is illustrated only diagrammatically. This fluorescence measuring instrument 40, however, is aligned with the surface 10 and detects fluorescence radiation originating from it. This corresponding fluorescence radiation can likewise be used for the evaluation of the optical characteristics of the surface.

The reference number 32 designates roughly diagrammatically a further light source which is likewise used for the illumination of the surface 10. The surface can be illuminated at a second angle by means of this further light source. In this case the light source is arranged in such a way that the light issuing from the light source 32 can also pass through the filter wheel 20 and thus a specified filter. Light can be directed directly onto the measurement spot by further optical elements such as lenses, diaphragms, beam diffusors or beam splitters (not shown in the figure). The reference number 57 refers to a beam splitter.

FIG. 2 is a diagrammatic illustration of a filter wheel 20. It will be seen that this filter wheel has a plurality of filter elements 14a, 14b, 14c, . . . which are all arranged in this case along a specific peripheral line K. As mentioned, the individual filter elements are in each case preferably band-pass filters which allow only a specified spectral portion of the light to be transmitted.

FIG. 3 is a perspective illustration of the filter wheel 20 shown in FIG. 2. In this case too, the annular arrangement of the individual filter elements is again evident.

FIG. 4 is an enlarged illustration of the filter wheel shown in FIG. 3. It will be seen that in this case the filters are arranged in each case in recesses 52. The recesses are separated from one another by means of webs 54. It is advantageous for the recesses or cut-away portions 52 respectively to be completely deburred. It is preferable for cuttings to be no longer present in the individual recesses. The webs can be used for the simple positioning or adhesion or snapping-in of the filters or even to prevent an optical crosstalk between the filters. In the case of a further advantageous embodiment the complete underside (i.e. the side facing towards the surface 10) of the filter wheel 20 or the carrier 20 respectively is kept in black and preferably in a matt surface. In this way, it is possible for measurement results not to be (especially adversely) affected by this surface.

The reference number 56 designates an alignment element by which a specific rotational setting of the filter wheel can be determined. This can be for example a mirror element or metallic element which allows the detection of a signal in a specified position, so that this rotational setting can be allocated in a purposeful manner.

The Applicants reserve the right to claim all the features disclosed in the application documents as being essential to the invention, insofar as they are novel either individually or in combination as compared with the prior art.

What claimed is:

1. An apparatus for the investigation of optical surface properties of a layer of paint with a housing, a light source which directs light through an opening in an optic block onto a surface to be investigated, with a first detector device which is arranged inside the optic block at a first pre-set angle with respect to the light beam radiated onto the surface by the light source, with a second detector device which is arranged inside the optic block at a second pre-set angle with respect to the light beam radiated onto the surface by the light source and preferably with a third detector device which is arranged inside the housing at a third pre-set angle with respect to the light beam radiated onto the surface by the light source, wherein the apparatus has at least two filter elements with optical properties which are different from each other which are arranged on a common carrier movable with respect to the light source, in such a way that each of these filter elements is optionally capable of being brought into a beam path between the light source and the surface, wherein the apparatus has a beam splitter device between the surface to be investigated and a detector device of the first through third detector devices, the beam splitter device having a single input for decoupling a portion of the light scattered off or reflected from the surface, and two outputs including a first output of the two outputs to an integral color measurement detector of the first through third detector devices and a second output of the two outputs to an imaging sensor.

2. An apparatus according to claim 1, wherein at least one filter element is a band-pass filter element.

3. An apparatus according to claim 1, wherein the light source is an LED, and in particular a white light LED.

4. An apparatus according to claim 1, wherein the light source covers the entire visible spectrum.

5. An apparatus according to claim 1, wherein the light source covers a portion of the UV range adjoining the visible spectrum of the light.

6. An apparatus according to claim 1, wherein the light source has a phosphorescent material.

7. An apparatus according to claim 6, wherein at least one filter element is capable of being brought into a beam path between the second light source and the surface.

8. An apparatus according to claim 1, wherein the carrier is a rotatable wheel.

9. An apparatus according to claim 1, wherein the apparatus has a second light source which directs light onto the surface to be investigated.

10. An apparatus according to claim 1, wherein the apparatus has a fluorescence measuring instrument.

11. An apparatus according to claim 10, wherein the fluorescence measuring instrument records radiation originating in the surface at least in part.

12. An apparatus according to claim 1, wherein the at least two filter elements with optical properties which are different from each other are designed in such a way that if they were positioned in succession in the beam path they would allow substantially no light to pass in their joint operation.

13. An apparatus according to claim 1, further comprising an optical measurement space, wherein the optical measurement space, with the exception of the opening by way of which light is radiated onto the surface to be investigated, has no further openings through which from the outside or ambient light respectively can enter the housing.

14. An apparatus according to claim 13, wherein the first, second, and third detector devices detect radiation of the light beam that occurs in the optical measurement space, wherein the apparatus further comprises a channel through which radiation at least one of scattered or reflected is received by the first, second, and third detector devices.

15. An apparatus according to claim 14, wherein the channel passes through a wall of the housing, permitting the detector devices to be adjacent each other.

16. An apparatus according to claim 1, wherein at least one of the first, second, or third detector devices is used for determining color properties of the surface.

17. An apparatus according to claim 1, wherein a surface to be investigated includes at least one of an effect-pigmented surface or a layer of paint of a vehicle body.

18. An apparatus according to claim 1, wherein for a measurement of fluorescence filters with an optical density of at least 5 are used.

19. An apparatus according to claim 1, wherein the beam splitter is constructed and arranged to decouple the beam path for measuring an intensity of illumination or a spectrum.

20. An apparatus according to claim 1, wherein a combination of the filter and another beam splitter directs the light from the light source to the layer of paint.

21. An apparatus according to claim 1, comprising three and only three detector devices, including the first, second, and third detector devices.

22. A method of investigating optical surface properties of a layer of paint, wherein light is radiated by means of a light source through an opening in an optic block onto a surface to be investigated and the light reflected and/or scattered by the surface as a consequence of this radiation is detected with a first detector device at a first pre-set angle with respect to the light beam radiated from the light source onto the surface, is detected with a second detector device at a second pre-set angle with respect to the light beam radiated from the light source onto the surface and is preferably detected by means of a third detector device at a third pre-set angle with respect to the light beam radiated from the light source onto the surface, wherein, while the method is carried out, at least two filter elements with mutually different optical properties, which are arranged on a common carrier movable with respect to the light source, are brought into a beam path between the light source and the surface in a manner staggered in time, so that only one filter element is present in this beam path in each case, and wherein a beam splitter device is positioned between the surface and at least one detector device of the first through third detector devices, the beam splitter device having a single input for decoupling a portion of the light scattered off or reflected from the surface, and two outputs including a first output of the two outputs to an integral color measurement detector of the first through third detector devices and a second output of the two outputs to an imaging sensor.

23. A method according to claim 22, wherein fluorescence radiation is also detected at least for a time.

24. A method according to claim 22, wherein the surface to be investigated is also illuminated by means of a second light source.

25. An apparatus according to claim 22, wherein a surface to be investigated includes at least one of an effect-pigmented surface or a layer of paint of a vehicle body.

* * * * *